United States Patent
Zhang et al.

(10) Patent No.: US 10,334,849 B2
(45) Date of Patent: Jul. 2, 2019

(54) SALTS OF CARBOXYLIC ACID HERBICIDES

(71) Applicant: Monsanto Technology LLC, St. Louis, MO (US)

(72) Inventors: Junhua Zhang, Chesterfield, MO (US); Daniel R. Wright, St. Louis, MO (US); William Abraham, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 420 days.

(21) Appl. No.: 14/354,287

(22) PCT Filed: Oct. 26, 2012

(86) PCT No.: PCT/US2012/062059
§ 371 (c)(1),
(2) Date: Apr. 25, 2014

(87) PCT Pub. No.: WO2013/063357
PCT Pub. Date: May 2, 2013

(65) Prior Publication Data
US 2014/0309114 A1   Oct. 16, 2014

Related U.S. Application Data

(60) Provisional application No. 61/551,764, filed on Oct. 26, 2011.

(51) Int. Cl.
*A01N 43/60* (2006.01)
*A01N 43/50* (2006.01)
*A01N 37/40* (2006.01)
*A01N 39/04* (2006.01)
*A01N 43/40* (2006.01)
*A01N 43/84* (2006.01)
*A01N 57/20* (2006.01)

(52) U.S. Cl.
CPC ............. *A01N 43/60* (2013.01); *A01N 37/40* (2013.01); *A01N 39/04* (2013.01); *A01N 43/40* (2013.01); *A01N 43/50* (2013.01); *A01N 43/84* (2013.01); *A01N 57/20* (2013.01)

(58) Field of Classification Search
CPC ........ A01N 43/40; A01N 43/50; A01N 43/60; A01N 43/84; A01N 37/40; A01N 39/04; A01N 57/20
USPC ........ 504/128, 225, 235, 275; 544/358, 401, 544/403, 87; 546/184, 186, 242, 248; 548/335.1, 343.5
See application file for complete search history.

(56) References Cited

U.S. PATENT DOCUMENTS

| | | |
|---|---|---|
| 2,505,059 A | 4/1950 | Moore |
| 3,013,054 A | 12/1961 | Richter |
| 3,276,856 A | 10/1966 | Esposito et al. |
| 3,594,151 A | 7/1971 | Sprayberry et al. |
| 3,600,407 A | 8/1971 | Levin et al. |
| 3,713,404 A | 1/1973 | Lavo et al. |
| 3,751,239 A | 8/1973 | McNulty et al. |
| 3,799,758 A | 3/1974 | Franz |
| 3,852,340 A | 12/1974 | Reck et al. |
| 3,870,732 A | 3/1975 | Hokama |
| 3,910,374 A | 10/1975 | Hokama |
| 3,923,849 A | 12/1975 | Hokama |
| 4,022,610 A | 5/1977 | Hokama |
| 4,405,531 A | 9/1983 | Franz |
| 4,445,927 A | 5/1984 | Gimesi et al. |
| 4,534,783 A | 8/1985 | Beestman |
| 4,546,196 A | 10/1985 | Luteri et al. |
| H0000303 H | 7/1987 | Malik et al. |
| 4,692,184 A | 9/1987 | Lee |
| 4,729,781 A | 3/1988 | Williams |
| 4,936,900 A | 6/1990 | Hyson |
| 4,936,901 A | 6/1990 | Surgant, Sr. et al. |
| 5,004,863 A | 4/1991 | Umbeck |
| 5,015,580 A | 5/1991 | Christou et al. |
| 5,035,738 A | 7/1991 | Burns et al. |
| 5,152,823 A | 10/1992 | Albercht et al. |
| 5,159,135 A | 10/1992 | Umbeck |
| 5,175,353 A | 12/1992 | Jones et al. |
| 5,221,319 A | 6/1993 | Van Haften et al. |
| 5,229,354 A | 7/1993 | Narayanan et al. |
| 5,229,355 A | 7/1993 | Chaudhuri et al. |
| 5,231,070 A | 7/1993 | Narayanan et al. |
| 5,250,500 A | 10/1993 | Jones et al. |
| 5,266,553 A | 11/1993 | Champion et al. |
| 5,283,228 A | 2/1994 | Narayanan et al. |
| 5,317,003 A | 5/1994 | Kassebaum et al. |
| 5,384,253 A | 1/1995 | Krzyzek et al. |
| 5,416,011 A | 5/1995 | Hinchee et al. |
| 5,434,783 A | 7/1995 | Pal et al. |
| 5,436,223 A | 7/1995 | Mulqueen et al. |
| 5,463,174 A | 10/1995 | Moloney et al. |

(Continued)

FOREIGN PATENT DOCUMENTS

AU      10073/92 B      10/1992
AU    2005221166 A1     9/2005
(Continued)

OTHER PUBLICATIONS

L.A. Cohen et al. (J. Heterocyclic Chemistry, vol. 28, Nov. 1991, pp. 1819-1820).*

(Continued)

*Primary Examiner* — Johann R Richter
*Assistant Examiner* — Courtney A Brown
(74) *Attorney, Agent, or Firm* — Stinson LLP; Erin C. Robert

(57) ABSTRACT

Amine salts of certain herbicides that in free acid form include at least one carboxylic acid moiety are described. Herbicide salts comprising the cation of various imidazole, piperazine, piperidine, and morpholine compounds are provided. The herbicide amine salts described are suitable for formulation into herbicidal application mixtures and/or stable concentration compositions that exhibit acceptable volatility characteristics upon application.

24 Claims, No Drawings

(56) References Cited

U.S. PATENT DOCUMENTS

| | | | |
|---|---|---|---|
| 5,508,184 | A | 4/1996 | Negrutiu et al. |
| 5,518,908 | A | 5/1996 | Corbin et al. |
| 5,538,880 | A | 7/1996 | Lundquist et al. |
| 5,550,318 | A | 8/1996 | Adams et al. |
| 5,565,409 | A | 10/1996 | Sato et al. |
| 5,569,834 | A | 10/1996 | Hinchee et al. |
| 5,591,616 | A | 1/1997 | Hiei et al. |
| 5,631,152 | A | 5/1997 | Fry et al. |
| 5,668,085 | A | 9/1997 | Forbes et al. |
| 5,670,454 | A | 9/1997 | Grossmann et al. |
| 5,703,015 | A | 12/1997 | Berger et al. |
| 5,733,848 | A | 5/1998 | Luteri |
| 5,750,468 | A | 5/1998 | Wright et al. |
| 5,824,877 | A | 10/1998 | Hinchee et al. |
| 5,834,006 | A | 11/1998 | Smith et al. |
| 5,877,112 | A | 3/1999 | Roberts |
| 5,883,046 | A | 3/1999 | Luteri |
| 5,883,048 | A | 3/1999 | Morre et al. |
| 5,965,487 | A | 10/1999 | Flahive |
| 5,981,840 | A | 11/1999 | Zhao et al. |
| 5,998,332 | A | 12/1999 | Sato et al. |
| 6,030,923 | A | 2/2000 | Okano et al. |
| 6,060,432 | A | 5/2000 | Adams et al. |
| 6,063,733 | A | 5/2000 | Berger et al. |
| 6,107,249 | A | 8/2000 | Wikeley |
| 6,121,199 | A | 9/2000 | Berger et al. |
| 6,133,199 | A | 10/2000 | Soula et al. |
| 6,160,208 | A | 12/2000 | Lundquist et al. |
| 6,177,414 | B1 | 1/2001 | Tomalia et al. |
| 6,228,807 | B1 | 5/2001 | Kuchikata et al. |
| 6,245,713 | B1 | 6/2001 | Brinker et al. |
| 6,277,788 | B1 | 8/2001 | Wright |
| 6,300,323 | B1 | 10/2001 | Haga et al. |
| 6,337,078 | B1 | 1/2002 | Levy |
| 6,384,301 | B1 | 5/2002 | Martinell et al. |
| 6,399,861 | B1 | 6/2002 | Anderson et al. |
| 6,403,865 | B1 | 6/2002 | Koziel et al. |
| 6,410,783 | B1 | 6/2002 | Peterson et al. |
| 6,417,140 | B1 | 7/2002 | Patel |
| 6,436,874 | B1 | 8/2002 | Kuah et al. |
| 6,455,473 | B2 | 9/2002 | Wright |
| RE37,866 | E | 10/2002 | Wright et al. |
| 6,500,783 | B1 | 12/2002 | Bryson et al. |
| 6,569,809 | B1 | 5/2003 | Sato et al. |
| 6,579,831 | B1 | 6/2003 | Harwell |
| 6,586,367 | B2 | 7/2003 | Lee et al. |
| 6,677,276 | B1 | 1/2004 | Hacker et al. |
| 6,713,433 | B2 | 3/2004 | Jimoh |
| 6,723,681 | B2 | 4/2004 | Hacker et al. |
| 6,774,087 | B1 | 8/2004 | Nakayama et al. |
| 6,906,004 | B2 | 6/2005 | Parrish et al. |
| 6,939,555 | B2 | 9/2005 | Volgas et al. |
| 7,135,437 | B2 | 11/2006 | Pallas et al. |
| 7,223,718 | B2 | 5/2007 | Smiley |
| 7,431,845 | B2 | 10/2008 | Manek et al. |
| 7,695,541 | B1 | 4/2010 | Frizzell et al. |
| 2002/0107149 | A1 | 8/2002 | Volgas et al. |
| 2002/0123430 | A1 | 9/2002 | Xu et al. |
| 2002/0155953 | A1 | 10/2002 | Brigance |
| 2003/0004063 | A1 | 1/2003 | Jimoh |
| 2003/0022791 | A1 | 1/2003 | Asrar et al. |
| 2003/0104943 | A1 | 6/2003 | Lennon et al. |
| 2004/0077499 | A1 | 4/2004 | Graham et al. |
| 2004/0138176 | A1 | 7/2004 | Miles |
| 2005/0026780 | A1 | 2/2005 | Parrish |
| 2006/0019828 | A1 | 1/2006 | Becher et al. |
| 2006/0040828 | A1 | 2/2006 | Mao et al. |
| 2006/0270556 | A1 | 11/2006 | Wright et al. |
| 2007/0093462 | A1 | 4/2007 | Rogers et al. |
| 2007/0149409 | A1 | 6/2007 | Burnet et al. |
| 2007/0184980 | A1 | 8/2007 | Roberts et al. |
| 2007/0259789 | A1 | 11/2007 | Huchet et al. |
| 2008/0119361 | A1 | 5/2008 | Feng et al. |
| 2008/0153706 | A1 | 6/2008 | Frisch et al. |
| 2008/0182773 | A1 | 7/2008 | Gauweiler et al. |
| 2008/0207452 | A1 | 8/2008 | Kramer et al. |
| 2008/0207453 | A1 | 8/2008 | Kramer et al. |
| 2009/0041813 | A1 | 2/2009 | Bouillo et al. |
| 2009/0062127 | A1 | 3/2009 | Liu |
| 2009/0093366 | A1 | 4/2009 | Wright et al. |
| 2009/0170702 | A1 | 7/2009 | Yoshii et al. |
| 2010/0113274 | A1 | 5/2010 | Hemminghaus et al. |
| 2010/0273654 | A1 | 10/2010 | Li et al. |
| 2010/0331182 | A1 | 12/2010 | Zhang et al. |
| 2011/0019652 | A1 | 1/2011 | Atwal |
| 2011/0034332 | A1 | 2/2011 | Becher et al. |
| 2011/0275517 | A1 | 11/2011 | Satchivi et al. |
| 2012/0142532 | A1 | 6/2012 | Wright et al. |
| 2012/0184434 | A1 | 7/2012 | Xu et al. |
| 2014/0171321 | A1 | 6/2014 | Wright et al. |
| 2014/0249026 | A1 | 9/2014 | Hemminghaus et al. |
| 2015/0164082 | A1 | 6/2015 | MacInnes |
| 2016/0366878 | A1 | 12/2016 | Wright et al. |

FOREIGN PATENT DOCUMENTS

| | | | |
|---|---|---|---|
| AU | 2010202620 | A1 | 7/2010 |
| CA | 1293974 | C | 1/1992 |
| CA | 2340240 | A1 | 2/2000 |
| CA | 2729738 | A1 | 1/2010 |
| CN | 1513326 | A | 7/2004 |
| DE | 4030687 | A1 | 5/1991 |
| DE | 19836737 | A1 | 5/1991 |
| DE | 19836660 | | 2/2000 |
| DE | 19836684 | | 2/2000 |
| DE | 19836700 | | 2/2000 |
| EP | 290416 | A2 | 6/1993 |
| EP | 360441 | A1 | 4/1994 |
| EP | 0375624 | B1 | 2/1995 |
| EP | 0808569 | A1 | 11/1997 |
| EP | 1023832 | A1 | 8/2000 |
| EP | 2 308 309 | A1 | 4/2011 |
| GB | 851008 | | 10/1960 |
| GB | 851008 | A | 10/1960 |
| GB | 1262123 | | 2/1972 |
| GB | 2267825 | A | 12/1993 |
| RU | 2208930 | C1 | 7/2003 |
| RU | 2366176 | C2 | 9/2009 |
| RU | 2384064 | C1 | 3/2010 |
| RU | 2395203 | C1 | 7/2010 |
| RU | 2408188 | C1 | 1/2011 |
| WO | 92/12637 | A1 | 9/1992 |
| WO | 95/16351 | A1 | 6/1995 |
| WO | 97/31535 | A2 | 9/1997 |
| WO | 99/00013 | A2 | 1/1999 |
| WO | 99/05914 | | 2/1999 |
| WO | 00/05951 | | 2/2000 |
| WO | 00/05952 | | 2/2000 |
| WO | 00/08936 | A1 | 2/2000 |
| WO | 00/15037 | A1 | 3/2000 |
| WO | 00/30451 | A1 | 6/2000 |
| WO | 00/30452 | | 6/2000 |
| WO | 00/64257 | A1 | 11/2000 |
| WO | 00/67571 | A1 | 11/2000 |
| WO | 01/17358 | A1 | 3/2001 |
| WO | 01/35740 | A2 | 5/2001 |
| WO | 01/89302 | A2 | 11/2001 |
| WO | 02/21924 | A2 | 3/2002 |
| WO | 02/096199 | A2 | 12/2002 |
| WO | 02/102153 | A2 | 12/2002 |
| WO | 03/013241 | A1 | 2/2003 |
| WO | 2003024218 | A1 | 3/2003 |
| WO | 2004/093546 | A1 | 11/2004 |
| WO | 2005/087007 | A1 | 9/2005 |
| WO | 2005/115144 | A1 | 12/2005 |
| WO | 2007/110355 | A2 | 10/2007 |
| WO | 2008/030749 | A2 | 3/2008 |
| WO | 2008/101818 | A2 | 8/2008 |
| WO | 2008106118 | A3 | 9/2008 |
| WO | WO 2008106118 | A2 * | 9/2008 ............ A01N 25/02 |
| WO | 2009/060026 | A2 | 5/2009 |
| WO | 2010/046422 | A2 | 4/2010 |
| WO | 2010071936 | A1 | 7/2010 |
| WO | 2010102102 | A1 | 9/2010 |

(56) References Cited

FOREIGN PATENT DOCUMENTS

| | | |
|---|---|---|
| WO | 2010147966 A1 | 12/2010 |
| WO | 2011/019652 A2 | 2/2011 |
| WO | 2011019652 A2 | 2/2011 |
| WO | 2011026800 A2 | 3/2011 |
| WO | 2011039172 A2 | 4/2011 |
| WO | 2011082162 A1 | 7/2011 |
| WO | 2012040785 A1 | 4/2012 |
| WO | 2012/104237 A2 | 8/2012 |
| WO | 2012/163824 A1 | 12/2012 |
| WO | 2013063357 A3 | 2/2013 |
| WO | 2013/184622 A3 | 12/2013 |
| WO | 2014134235 A1 | 9/2014 |
| ZA | 8907205 | 6/1990 |

OTHER PUBLICATIONS

G. Theilig et al. (Chemische Berichte, vol. 86, Jan. 1953, pp. 88-95).*
G. Halschke et al. (Chemische Berichte, vol. 92, Jan. 1959, pp. 92-96).*
SIGMA Product Information 1-Methylimidazole Product No. M 8878 [online, retrieved on Nov. 8, 2017]. Retrieved from the Internet< https://www.sigmaaldrich.com/content/dam/sigma-aldrich/docs/Sigma/Product_Information_Sheet/1/m8878pis.pdf>.*
SIGMA-Aldrich Product Information Imidazole, for molecular biology Catalog No. I5513 [online, retrieved on Nov. 8, 2017]. Retrieved from the Internet< https://www.sigmaaldrich.com/content/dam/sigma-aldrich/docs/Sigma/Product_Information_Sheet/2/i5513pis.pdf.*
Behrens, et al., "Dicamba Volatility," 1979, Weed Source, 27/5:486-493.
D'Sa, et al., "4,5-Dimethylimidazole: A Correction and Alternative Synthesis," 1991, J Heterocyclic Chem, 28, 1819-1920, XP055055998.
Duff, et al., "Identification of Carboxylic Acids: Use of N-Methylpiperazine and N-Phenylpiperazine," 1969, J Chem Ed, ACS, 46:388-390, XP009141119.
Giesemann, et al., "Untersuhungen über 1-Triphenylmethyl-imidazole, I," 1959, Chemische Berichte, 92:92-96, XP055056003.
Hatzios, et al., "Pelargonic Acid," 1998, WAASA Herbicide handbook, pp. 55-57, 3 pages, XP002953604.
Pernak, et al., "Ionic Liquids with Herbicidal Anions," 2011, Tetrahedron, 67:4838-4844, XP028227648.
Pernak, et al., "2,4-D Based Herbicidal Ionic Liquids," 2012, Tetrahedron, 68:4267-4273M XP028479458.
Prigot et al., "Derivatives of Piperazine. XXII. Piperazinium Salts for Utilization in Identification of Organic Acids," 1948, J Am Chem Soc, 70:2758-2759, XP055056011.
Theilig, G., et al., "Imidazolsynthesen mit Formamid (Formamid-Reaktionen, I. Mitteil.)," 1953, Chemische Berichte, 86:99-95, XP055056002.
International Preliminary Report on Patentability dated Apr. 29, 2014, in International PCT Application No. PCT/US2012/062059, 13 pages.
International Search Report and Written Opinion dated Jun. 14, 2013, in International PCT Application No. PCT/US2012/062059, 21 pages.
Gilchrist, T.L., Heterocyclic Chemistry, Second Ed., 1992, Longman Group United Kingdom, pp. 283-293, 13 pages.
Potts, K.T., Comprehensive Heterocyclic Chemistry, vol. 5, 1984, p. 284.
Wilkes, John S. et al., Dialkylimidazolium Chloroaluminate Melts: A New Class of Room-Temperature Ionic Liquids for Electrochemistry, Spectroscopy, and Synthesis, Inorg. Chem. 1982, 21, pp. 1263-1264.
Agrian, Buffer Protect, Westbridge Agricultural Products, http://www.agrian.com/labelcenter, downloaded Jan. 17, 2013, 2 pages.
Branham, B.E., et al., "Drift and Volatility of Broadleaf Herbicides," pp. 126-129.
Clarity®, Safety Data Sheet, BASF, Revised Aug. 14, 2006, 7 pages.

Climb® Alkalinity Agent, Wilbur-Ellis Company, CA Reg. No. 2935-50181, WA Reg. No. 2935-09001, F-091809-1, 2 pages.
Foy, C.L., et al., "Effect of Inhibitors and herbicides on Tricarboxylic Acid Cycle Substrate Oxidation by Isolated Cucumber Mitochondria," 1965, Weeds, 13/3:226-231.
Hall, J.K., et al., "Dicamba Mobility in Conventionally Tilled and Non-Tilled Soils," 1994, Soil & Tillage Res, 30:3-17.
Hartzler, B., "Dicamba Volatility," 2001, Weed Science Online, Iowa State University, Downloaded Mar. 27, 2014, 4 pages.
Hoefer, R.H., et al., "Absorption of Dicamba in Soybeans as Effected by Formulation and Suractants," 1979, North Central Weed Control Conference, Abstract, pp. 4-5.
Lupasol® Products, Technical Information, Feb. 2008, BASF, 12 pages.
Lupasol®, Polyethylenimines for Creative Connections, BASF, EVD 0116e Nov. 2005, pp. 6.
Material Safety Data Sheet regarding Amine 4 2,4-D Weed Killer prepared by Registrations and Regulatory Affairs, Date of Issue Dec. 14, 2012, 3 pages.
Material Safety Data Sheet, BANVEL II®, BASF, Revised Nov. 30, 2006, 5 pages.
Material Safety Data Sheet, BANVEL®, EPA Reg. No. 51036-289, BASF, Prepared Jul. 14, 1999, 3 pages.
Material Safety Data Sheet, DICAMBA 480 Manufacturing Concentrate, Reg. No. 24774, Syngenta Crop Protection Canada, Inc., MSDS Preparation Date Dec. 31, 2008, 6 pages.
Nialewaja, J.D., et al., "Salt Antagonism of Glyphosate," 1991, Weed Science, 39:622-628.
Nialewaja, J.D., et al., "2,4-D Amine Antagonism by Salts," 1991, Weed Technology, 514:873-880.
Owen, M.D.K., et al., "Evaluation of Nicosulfuron, Rimsulfuron, and Pyridate Applied Postemergence for Weed Control in Corn," 1995, NCWSS Research Report-V.52, Ames, IA, 149-152.
Peniuk, M.G., et al., "Absorption, Translocation, and Metabolosm are not the Basis for Differential Selectivity of Wild Mustart (Sinapis argensis L.)," 1992, WSSA Abstracts, No. 165, 32:55.
Petersen, P.J., et al., "Dicamba Absorption and Translocation as Influenced by Formulation and Surfactant," 1985, Weed Science, 33:717-720.
Poovaiah, B.W., et al., "Effects of Inorganic Salts on Tissue Permeability," 1976, Plant Physiol., 58:182-185.
Purdue, Herbicide Formulations (http://web.archive.org/web/*/http://www.agriculture.purdue.edu/fnr/html/faculty/holt/NRCASupplement.pdf) from 2007, 19 pages.
Quimby, P.C., Jr., et al., "Selectivity of Dicamba in Wheat and Wild Buckwheat," 1971, Weed Science, 19/5:598-601.
Ramirez-Ortega, R., et al., "Enhancement Effect of N, P and K on Glyphosate for Broomrape (Orobanche crenata Forsk.) Control in Faba Bean (Vicia faba L.)," 1992, FABIS Newsletter 31, pp. 37-39.
Safety Data Sheet—Clarity (Version 3.0), BASF The Chemical Company, May 2, 2013, 9 pages.
Sargent, J.A., "Chapter 10 Relatiohnship of Selectivity to Uptake and Movement," 1976, Herbicides, 2nd Ed, vol. 2, 303-312, 12 pages.
Scott, P.C., "Separation of Effects of Auxin and Ethylene in Pea Roots," 1970, Nature, 226:1366-1367.
Serafini, dicamba, diglycolamine salt (Clarity) Active Ingredient Registration 6/00, (http://pmep.cce.cornell.edu/profiles/herb-growthreg/dalapon-ethephon/diglycolamine/Diglycolamine_600.html), downloaded Apr. 6, 2014, 3 pages.
Sprankle, P., et al., Rapid Inactivation of Glyphosate in the Soil, 1975, Weed Science, 23/3:224-228.
Wauchope, R.D., et al, "The SCS/ARS/CES Pesticide Properties Database for Environmental Decision-Making," 1992, Rvws of Environ Contam and Toxic, 123:1-164.
Dion, H.M., et al., "Competitive Sorption Between Glyphoste and Inorganic Phosphate on Clay Minerals and Low Organic Matter Soils," 2001, J Radioanaly and Nucl Chem, 249/2:385-390.
Material Safety Data Sheet, Blend of Di-potassium Phosphate, Nitrogen, and Ag-Phite (DKP xtra), Product No. 3-18-20, Plant Food Systems, Inc., Undated, 1 page.

* cited by examiner

SALTS OF CARBOXYLIC ACID HERBICIDES

REFERENCE TO RELATED APPLICATION

The present application is the 371 National Stage Application of International Patent Application Serial No. PCT/US2012/062059, filed Oct. 26, 2012, which claims the benefit of U.S. Provisional Application Ser. No. 61/551,764, filed Oct. 26, 2011, the entire contents of which are incorporated herein by reference.

FIELD OF THE INVENTION

The present invention generally relates to various salts of carboxylic acid herbicides. In particular, the present invention is directed to amine salts of certain herbicides that in free acid form include at least one carboxylic acid moiety. The herbicide amine salts are suitable for formulation into herbicidal application mixtures and/or stable concentrate compositions that exhibit acceptable volatility characteristics upon application.

BACKGROUND OF THE INVENTION

Various herbicides in free acid form, such as many auxin herbicides, have at least one carboxylic acid moiety. Auxin herbicides having at least one carboxylic acid moiety include 3,6-dichloro-2-methoxybenzoic acid (dicamba); 2,4-dichlorophenoxyacetic acid (2,4-D); 4-(2,4 dichlorophenoxy)butanoic acid (2,4-DB); 2-(2,4-dichlorophenoxy)propanoic acid (dichloroprop); 2-(4-chloro-2-methylphenoxy)acetic acid (MCPA); 4-(4-chloro-2-methylphenoxy)butanoic acid (MCPB); 4-amino-3,6-dichloro-2-pyridinecarboxylic acid (aminopyralid); 3,6-dichloro-2-pyridinecarboxylic acid (clopyralid); 2-[(4-amino-3,5-dichloro-6-fluoro-2-pyridinyl)oxy]acetic acid (fluroxypyr); [(3,5,6-trichloro-2-pyridinyl)oxy]acetic acid (triclopyr); 2-(4-chloro-2-methylphenoxy)propanoic acid (mecoprop); 4-amino-3,5,6-trichloro-2-pyridinecarboxylic acid (picloram); 3,7-dichloro-8-quinolinecarboxylic acid (quinclorac); and 6-amino-5-chloro-2-cyclopropyl-4-pyrimidinecarboxylic acid (aminocyclopyrachlor). In particular, dicamba and 2,4-D have proven to be effective auxin herbicides.

Generally, synthetic auxin herbicides such as dicamba and 2,4-D mimic or act like natural auxin plant growth regulators. Auxin herbicides appear to affect cell wall plasticity and nucleic acid metabolism, which can lead to uncontrolled cell division and growth. The injury symptoms caused by auxin herbicides include epinastic bending and twisting of stems and petioles, leaf cupping and curling, and abnormal leaf shape and venation.

In order to provide enhanced solubility and increased herbicide loading for greater ease in formulation, conventional dicamba and other carboxylic acid auxin herbicide products are typically formulated as water-soluble salt solutions. For example, CLARITY (available from BASF) is a formulation containing the diglycolamine salt of dicamba and BANVEL (available from Arysta LifeScience North America LLC) is a formulation containing the dimethylamine salt of dicamba.

Off-site movement is sometimes associated with auxin herbicides. Volatile auxin herbicides like dicamba and 2,4-D can, under certain conditions of application, volatilize into the surrounding atmosphere and migrate from the application site to adjacent crop plants, such as soybeans and cotton, where contact damage to sensitive plants can occur. Typical symptoms of injury to crop plants include leaf cupping, leaf malformation, leaf necrosis, terminal bud kill and/or delayed maturity.

Some strategies to reduce herbicide volatilization have focused on encapsulation. In one approach, dicamba is absorbed into solid phase natural or synthetic polymers. However, the resulting particle sizes are typically not suitable for spray application and therefore limited to granular drop application. Micro-encapsulation in a polymer shell is also known in the art, but the relatively high solubility of dicamba and its salts precludes successful use of the technology in aqueous suspensions, and commercial dicamba micro-encapsulation products have not been developed.

Thus, a need persists for the identification of alternative salts of carboxylic acid herbicides that are suitable for formulation into herbicidal application mixtures and/or concentrate compositions that exhibit acceptable stability and compatibility characteristics. Preferably, the carboxylic acid herbicide salts exhibit low volatility in herbicide compositions that are efficacious, yet non-phytotoxic to sensitive crops located in areas adjacent to the target site and resist adverse effects to their volatility characteristics when tank mixed with other co-herbicides such as glyphosate.

SUMMARY OF THE INVENTION

The present invention is directed to herbicide salts comprising an anion of a carboxylic acid herbicide and a cation of a compound selected from the group consisting of:

(a) Formula I:

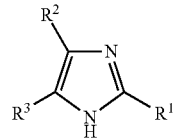

Formula I wherein $R^1$, $R^2$ and $R^3$ are independently hydrogen or substituted or unsubstituted hydrocarbyl;

(b) Formula II:

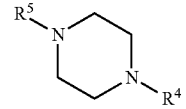

Formula II wherein $R^4$ and $R^5$ are independently hydrogen or substituted or unsubstituted hydrocarbyl, provided that when $R^5$ is hydrogen or an unsubstituted $C_1$-$C_6$ alkyl, then $R^4$ is not an aminoalkyl or when $R^4$ is hydrogen or an unsubstituted $C_1$-$C_6$ alkyl, then $R^5$ is not an aminoalkyl;

(c) Formula III:

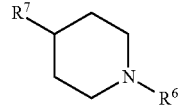

Formula III wherein $R^6$ is hydrogen, substituted or unsubstituted $C_1$-$C_{20}$ alkyl, substituted or unsubstituted $C_1$-$C_{20}$ alkanol, substituted or unsubstituted $C_5$-$C_{20}$ cycloalkyl, substituted or unsubstituted $C_3$-$C_{20}$ heterocycloalkyl, substituted or unsubstituted aryl, substituted or unsubstituted alkylaryl, or substituted or unsubstituted heteroaryl and $R^7$ is hydrogen, oxo, or unsubstituted or substituted hydrocarbyl, provided that when $R^6$ is an unsubstituted $C_1$-$C_6$ alkyl, then $R^7$ is not an aminoalkyl or when $R^7$ is hydrogen or an unsubstituted $C_1$-$C_6$ alkyl, then $R^6$ is not an aminoalkyl;

(d) Formula IV:

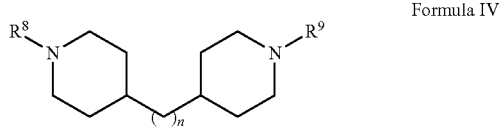

Formula IV wherein n is from 1 to about 20, from 1 to about 10, from about 3 to about 10, or from about 3 to about 6 (e.g., 3) and $R^8$ and $R^9$ are independently any substituent as defined for $R^7$;

(e) Formula V:

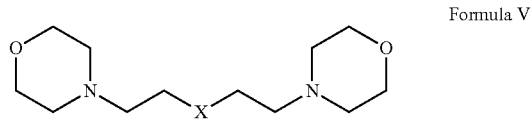

Formula V wherein X is O, $NR^{10}$ or S and $R^{10}$ is hydrogen or $C_{1-6}$ alkyl; and tautomers and mixtures thereof.

The present invention is further directed to herbicidal application mixtures comprising the herbicidal salts described herein useful for killing or controlling the growth of unwanted plants.

Other objects and features will be in part apparent and in part pointed out hereinafter.

DESCRIPTION OF THE PREFERRED EMBODIMENTS

In general, the present invention is directed to amine salts of carboxylic acid herbicides which, in free acid form, have at least one carboxylic acid moiety.

In accordance with the present invention, amine salts of carboxylic acid herbicides are provided that are suitable for formulation into herbicidal application mixtures and/or concentrate compositions that exhibit acceptable stability and compatibility characteristics. Herbicide salts are provided that are suitable for preparing stable, highly loaded herbicidal solutions, concentrates and/or emulsion concentrates. In accordance with some preferred embodiments, the herbicidal amine salts are selected so as to exhibit relatively low volatility. As compared to conventional herbicide salts known in the art, it is believed that some of the preferred herbicide salts of the present invention provide enhanced protection from offsite movement while maintaining comparably effective herbicidal efficacy on unwanted plants located in the target area. Further, herbicides salts are provided that are stable and resist adverse effects to their volatility characteristics upon mixing or formulating with other ingredients such as co-herbicides (e.g., glyphosate or glufosinate).

Typically, a herbicide salt of the present invention is derived from a carboxylic acid herbicide and a base compound (e.g., amine). For example, in one method, herbicide in free acid form is mixed with an amine base in water or other suitable solvent. As recognized by those skilled in the art, formation of the herbicide salt results from proton exchange between the carboxylic acid moiety and base.

The herbicide salts of the present invention comprise a carboxylate anion of a carboxylic acid herbicide. For example, in various embodiments, the herbicide salt may comprise the carboxylate anion of a herbicide selected from the group consisting of 3,6-dichloro-2-methoxybenzoic acid (dicamba); 2,4-dichlorophenoxyacetic acid (2,4-D); 4-(2,4 dichlorophenoxy)butanoic acid (2,4-DB); 2-(2,4-dichlorophenoxy)propanoic acid (dichloroprop); 2-(4-chloro-2-methylphenoxy)acetic acid (MCPA); 4-(4-chloro-2-methylphenoxy)butanoic acid (MCPB); 4-amino-3,6-dichloro-2-pyridinecarboxylic acid (aminopyralid); 3,6-dichloro-2-pyridinecarboxylic acid (clopyralid); 2-[(4-amino-3,5-dichloro-6-fluoro-2-pyridinyl)oxy]acetic acid (fluroxypyr); [(3,5,6-trichloro-2-pyridinyl)oxy]acetic acid (triclopyr); 2-(4-chloro-2-methylphenoxy)propanoic acid (mecoprop); 4-amino-3,5,6-trichloro-2-pyridinecarboxylic acid (picloram); 3,7-dichloro-8-quinolinecarboxylic acid (quinclorac); 6-amino-5-chloro-2-cyclopropyl-4-pyrimidinecarboxylic acid (aminocyclopyrachlor) and combinations thereof. In certain embodiments, the herbicide salt comprises the carboxylate anion of 3,6-dichloro-2-methoxybenzoic acid (dicamba) or 2,4-dichlorophenoxyacetic acid (2,4-D).

In accordance with the present invention, the herbicide salts further comprise a cation of various imidazole compounds, piperazine compounds, piperidine compounds, and morpholine compounds. Accordingly, as discussed in detail below, in various embodiments, the herbicide salt comprises an anion of a carboxylic acid herbicide and a cation of a compound selected from the group consisting of imidazole derivatives, piperazine derivatives, piperidine derivatives, and morpholine derivatives and mixtures thereof.

In particular embodiments, the herbicide salt of the present invention comprises a cation of an imidazole compound of Formula I:

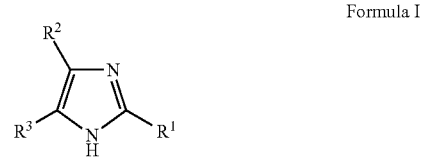

Formula I wherein $R^1$, $R^2$ and $R^3$ (i.e., the 2-, 4-, and/or 5-positions, respectively, as shown below) are independently hydrogen or substituted or unsubstituted hydrocarbyl. In accordance with some embodiments of the present invention, the cation derived from a compound of Formula I is a 2-, 4-, and/or 5-substituted imidazole cation (i.e., at least one of $R^1$, $R^2$ and $R^3$ are independently substituted or unsubstituted hydrocarbyl).

In general, the naming of imidazole moieties discussed herein follows conventional organic chemistry nomenclature. For purposes of clarity, the ring positions on an imidazole ring are numbered as shown below.

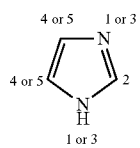

The carbon atom between the two nitrogen atoms is referred to as the 2-position. The two nitrogen atoms adjacent the 2-position carbon atom are each referred to as either the 1 or 3 position, and the remaining two carbon atoms are referred to as either the 4- or 5-position. These positions are determined according to the naming convention which uses the lowest possible numbers for the substituents. Further, it is recognized that tautomers of imidazole moieties may exist in equilibrium in solution. For simplicity, when discussing imidazole moieties herein, only one tautomeric form is named or shown, but it is understood that such name or structure represents the other tautomer(s) as well.

Without being bound by theory, in some instances, selection of higher hydrocarbyl substituents that are relatively more hydrophobic are believed to enhance the low volatility characteristics of the herbicide salt (e.g., ethyl is preferable over methyl and so on). However, should an aqueous herbicidal solution or formulation of the salt be desired, the substituents are also selected to ensure sufficient water solubility. Accordingly, in various embodiments, $R^1$, $R^2$ and $R^3$ are independently hydrogen, substituted or unsubstituted $C_1$-$C_{20}$ alkyl, substituted or unsubstituted $C_1$-$C_{20}$ alkanol, substituted or unsubstituted $C_5$-$C_{20}$ cycloalkyl, substituted or unsubstituted $C_3$-$C_{20}$ heterocycloalkyl, substituted or unsubstituted aryl, or substituted or unsubstituted heteroaryl.

In some embodiments, $R^1$ is a substituted or unsubstituted $C_1$-$C_{20}$ alkyl, substituted or unsubstituted $C_1$-$C_{20}$ alkanol, substituted or unsubstituted $C_5$-$C_{20}$ cycloalkyl, substituted or unsubstituted $C_3$-$C_{20}$ heterocycloalkyl, substituted or unsubstituted aryl, or substituted or unsubstituted heteroaryl. In these and other embodiments, $R^1$ is a substituted or unsubstituted $C_1$-$C_{10}$ alkyl, substituted or unsubstituted $C_1$-$C_{10}$ alkanol, substituted or unsubstituted $C_5$-$C_{10}$ cycloalkyl, substituted or unsubstituted $C_3$-$C_{10}$ heterocycloalkyl, substituted or unsubstituted aryl, or substituted or unsubstituted heteroaryl. In some embodiments, $R^1$ is a $C_1$-$C_6$ alkyl (preferably $C_2$-$C_6$ alkyl), $C_1$-$C_6$ alkanol, $C_5$-$C_6$ cycloalkyl, or aryl. Still in other embodiments, $R^1$ is a $C_1$-$C_6$ alkyl (preferably methyl, ethyl, isopropyl) or aryl (preferably phenyl).

Further, in various embodiments, $R^2$ and $R^3$ are independently hydrogen, substituted or unsubstituted $C_1$-$C_{10}$ alkyl, substituted or unsubstituted $C_1$-$C_{10}$ alkanol, substituted or unsubstituted $C_5$-$C_{10}$ cycloalkyl, substituted or unsubstituted $C_3$-$C_{10}$ heterocycloalkyl, substituted or unsubstituted aryl, or substituted or unsubstituted heteroaryl. In some embodiments, $R^2$ and $R^3$ are independently hydrogen or substituted or unsubstituted $C_1$-$C_{10}$ alkyl. In these and other embodiments, $R^2$ and $R^3$ are independently hydrogen or substituted or unsubstituted $C_1$-$C_6$ alkyl and more preferably $C_1$-$C_6$ alkyl such as methyl or ethyl.

When $R^1$, $R^2$ and/or $R^3$ of Formula I is a substituted group such as substituted hydrocarbyl, substituted alkyl, substituted alkanol, substituted cycloalkyl, substituted heterocycloalkyl, substituted aryl, and substituted heteroaryl, the substituted group preferably includes one or more substituents selected from group consisting of alkyl, alkoxy, hydroxyl, oxy, phenyl, carboxyl, and amino. Even more preferably, these substituted groups are substituted with one or more substituents selected from group consisting of $C_{1-6}$ alkyl, $C_{1-6}$ alkoxy, hydroxyl, oxy, phenyl, carboxyl, and amino.

In other embodiments, the herbicide salt of the present invention comprises a cation of a piperazine compound. In particular, the herbicide salt comprises a cation of a compound of Formula II:

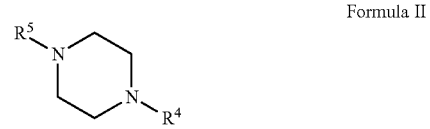

Formula II wherein $R^4$ and $R^5$ are independently hydrogen or substituted or unsubstituted hydrocarbyl, provided that when $R^5$ is hydrogen or an unsubstituted $C_1$-$C_6$ alkyl, then $R^4$ is not an aminoalkyl or when $R^4$ is hydrogen or an unsubstituted $C_1$-$C_6$ alkyl, then $R^5$ is not an aminoalkyl.

In some embodiments, only one nitrogen atom is substituted on the piperazine ring (e.g., $R^5$ is hydrogen). In these embodiments, $R^4$ is a substituted or unsubstituted $C_1$-$C_{20}$ alkyl (other than an aminoalkyl), substituted or unsubstituted $C_1$-$C_{20}$ alkanol, substituted or unsubstituted $C_5$-$C_{20}$ cycloalkyl, substituted or unsubstituted $C_3$-$C_{20}$ heterocycloalkyl, substituted or unsubstituted aryl, or substituted or unsubstituted heteroaryl. In these and other embodiments, $R^4$ is a substituted or unsubstituted $C_1$-$C_{10}$ alkyl (other than an aminoalkyl), substituted or unsubstituted $C_1$-$C_{10}$ alkanol, substituted or unsubstituted $C_5$-$C_{10}$ cycloalkyl, substituted or unsubstituted $C_3$-$C_{10}$ heterocycloalkyl, substituted or unsubstituted aryl, or substituted or unsubstituted heteroaryl. In some embodiments, $R^4$ is a substituted or unsubstituted $C_1$-$C_6$ alkyl (other than an aminoalkyl), substituted or unsubstituted $C_1$-$C_6$ alkanol, or substituted or unsubstituted $C_5$-$C_6$ cycloalkyl. In particular embodiments, $R^4$ is a $C_1$-$C_6$ alkyl (preferably ethyl, propyl, butyl, pentyl, or hexyl), $C_1$-$C_6$ alkanol (preferably hydroxyethyl), or a $C_5$-$C_6$ cycloalkyl (preferably cyclohexyl).

In other embodiments, both nitrogen atoms of the piperazine ring are substituted (i.e., $R^4$ and $R^5$ are not hydrogen). In these embodiments, $R^4$ and $R^5$ are independently substituted or unsubstituted $C_1$-$C_{20}$ alkyl, substituted or unsubstituted $C_1$-$C_{20}$ alkanol, substituted or unsubstituted $C_5$-$C_{20}$ cycloalkyl, substituted or unsubstituted $C_3$-$C_{20}$ heterocycloalkyl, substituted or unsubstituted aryl, or substituted or unsubstituted heteroaryl, provided that when $R^5$ is an unsubstituted $C_1$-$C_6$ alkyl, then $R^4$ is not an aminoalkyl or when $R^4$ is an unsubstituted $C_1$-$C_6$ alkyl, then $R^5$ is not an aminoalkyl. In these and other embodiments, $R^4$ and $R^5$ are independently substituted or unsubstituted $C_1$-$C_{10}$ alkyl, substituted or unsubstituted $C_1$-$C_{10}$ alkanol, substituted or unsubstituted $C_5$-$C_{10}$ cycloalkyl, substituted or unsubstituted $C_3$-$C_{10}$ heterocycloalkyl, substituted or unsubstituted aryl, or substituted or unsubstituted heteroaryl, provided that when $R^5$ is an unsubstituted $C_1$-$C_6$ alkyl, then $R^4$ is not an aminoalkyl or when $R^4$ is an unsubstituted $C_1$-$C_6$ alkyl, then $R^5$ is not an aminoalkyl. In some embodiments, $R^4$ and $R^5$ are independently $C_1$-$C_6$ substituted or unsubstituted alkyl, $C_1$-$C_6$ substituted or unsubstituted alkanol, substituted or unsubstituted $C_5$-$C_6$ cycloalkyl or substituted or unsubstituted $C_3$-$C_6$ heterocycloalkyl, provided that when $R^5$ is an unsubstituted $C_1$-$C_6$ alkyl, then $R^4$ is not an aminoalkyl or when $R^4$ is an unsubstituted $C_1$-$C_6$ alkyl, then $R^5$ is not an aminoalkyl. In particular embodiments, $R^4$ and $R^5$ are independently a $C_1$-$C_6$ alkyl (preferably methyl, ethyl, propyl, or butyl), $C_1$-$C_6$ alkanol (preferably hydroxyethyl), or a $C_5$-$C_6$ cycloalkyl (preferably cyclohexyl). In certain embodiments, the $R^4$ and $R^5$ are the same substituent (e.g., $R^4$ and $R^5$ are both methyl). In various embodiments, $R^4$ and $R^5$ are not aminoalkyl.

When $R^4$ and/or $R^5$ of Formula II is a substituted group such as substituted hydrocarbyl, substituted alkyl, substituted alkanol, substituted cycloalkyl, substituted heterocycloalkyl, substituted aryl, and substituted heteroaryl, the substituted group preferably includes one or more substituents selected from group consisting of alkyl, alkoxy, hydroxyl, oxy, phenyl, carboxyl, and amino. Even more preferably, these substituted groups are substituted with one or more substituents selected from group consisting of $C_{1-6}$ alkyl, $C_{1-6}$ alkoxy, hydroxyl, oxy, phenyl, carboxyl, and amino.

In other embodiments, the herbicide salt of the present invention comprises a cation of a piperidine compound. In particular, the herbicide salt comprises a cation of a compound of Formula III:

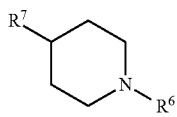

Formula III wherein $R^6$ is substituted or unsubstituted $C_1$-$C_{20}$ alkyl, substituted or unsubstituted $C_1$-$C_{20}$ alkanol, substituted or unsubstituted $C_5$-$C_{20}$ cycloalkyl, substituted or unsubstituted $C_3$-$C_{20}$ heterocycloalkyl, substituted or unsubstituted aryl, substituted or unsubstituted alkylaryl, or substituted or unsubstituted heteroaryl and $R^7$ is hydrogen, oxo, or unsubstituted or substituted hydrocarbyl, provided that when $R^6$ is an unsubstituted $C_1$-$C_6$ alkyl, then $R^7$ is not an aminoalkyl or when $R^7$ is hydrogen or an unsubstituted $C_1$-$C_6$ alkyl, then $R^6$ is not an aminoalkyl.

In various embodiments, $R^6$ is a substituted or unsubstituted $C_1$-$C_{10}$ alkyl, substituted or unsubstituted $C_1$-$C_{10}$ alkanol, substituted or unsubstituted $C_5$-$C_{10}$ cycloalkyl, substituted or unsubstituted $C_3$-$C_{10}$ heterocycloalkyl, substituted or unsubstituted aryl, substituted or unsubstituted alkylaryl, or substituted or unsubstituted heteroaryl, provided that when $R^6$ is an unsubstituted $C_1$-$C_6$ alkyl, then $R^7$ is not an aminoalkyl or when $R^7$ is hydrogen or an unsubstituted $C_1$-$C_6$ alkyl, then $R^6$ is not an aminoalkyl. In these and other embodiments, $R^6$ is a substituted or unsubstituted $C_1$-$C_6$ alkyl, substituted or unsubstituted $C_1$-$C_6$ alkanol, $C_5$-$C_6$ cycloalkyl, $C_3$-$C_6$ heterocycloalkyl, aryl or alkylaryl, provided that when $R^6$ is an unsubstituted $C_1$-$C_6$ alkyl, then $R^7$ is not an aminoalkyl or when $R^7$ is hydrogen or an unsubstituted $C_1$-$C_6$ alkyl, then $R^6$ is not an aminoalkyl. In particular embodiments, $R^6$ is a $C_1$-$C_6$ alkyl (preferably methyl, ethyl, propyl, isobutyl), $C_1$-$C_6$ alkanol (preferably hydroxyethyl), $C_3$-$C_6$ heterocycloalkyl (preferably piperdyl), aryl (preferably phenyl), or alkylaryl (preferably benzyl), provided that when $R^6$ is an unsubstituted $C_1$-$C_6$ alkyl, then $R^7$ is not an aminoalkyl. In various embodiments, $R^6$ is not an aminoalkyl.

Further, in various embodiments, $R^7$ is hydrogen, oxo, substituted or unsubstituted $C_1$-$C_{20}$ alkyl, substituted or unsubstituted $C_5$-$C_{20}$ cycloalkyl, substituted or unsubstituted $C_3$-$C_{20}$ heterocycloalkyl, substituted or unsubstituted aryl, or substituted or unsubstituted heteroaryl. More particularly, in these and other embodiments $R^7$ is hydrogen, oxo, substituted or unsubstituted $C_1$-$C_{10}$ alkyl, substituted or unsubstituted $C_5$-$C_{10}$ cycloalkyl, substituted or unsubstituted $C_3$-$C_{10}$ heterocycloalkyl, substituted or unsubstituted aryl, or substituted or unsubstituted heteroaryl. In certain embodiments, $R^7$ is hydrogen or oxo. In various embodiments, $R^7$ is not an aminoalkyl.

When $R^6$ and/or $R^7$ of Formula III is a substituted group such as substituted alkyl, substituted alkanol, substituted cycloalkyl, substituted heterocycloalkyl, substituted aryl, and substituted heteroaryl, the substituted group preferably includes one or more substituents selected from group consisting of alkyl, alkoxy, hydroxyl, oxy, phenyl, carboxyl, and amino. Even more preferably, these substituted groups are substituted with one or more substituents selected from group consisting of $C_{1-6}$ alkyl, $C_{1-6}$ alkoxy, hydroxyl, oxy, phenyl, carboxyl, and amino.

In various embodiments, the herbicide salt of the present invention comprises a cation of a bispiperidine compound. In particular, the herbicide salt comprises a cation of a compound of Formula IV:

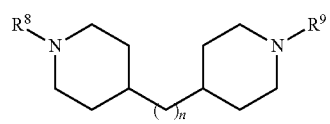

Formula IV wherein n is from 1 to about 20, from 1 to about 10, from about 3 to about 10, or from about 3 to about 6 (e.g., 3) and $R^8$ and $R^9$ are independently any substituent as defined above for $R^7$ in Formula III. For example, in various embodiments, $R^8$ and $R^9$ are each methyl or hydrogen.

In other embodiments, the herbicide salt of the present invention comprises a cation of a bismorpholine compound. In particular, the herbicide salt comprises a cation of a compound of Formula V:

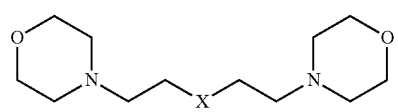

Formula V wherein X is O, $NR^{10}$ or S and $R^{10}$ is hydrogen or $C_{1-6}$ alkyl.

In certain embodiments, the herbicide salt of the present invention comprises a cation of a compound selected from the group consisting of:

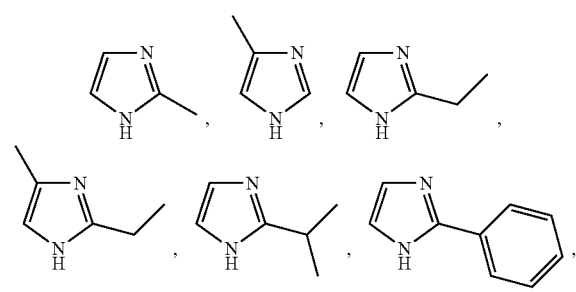

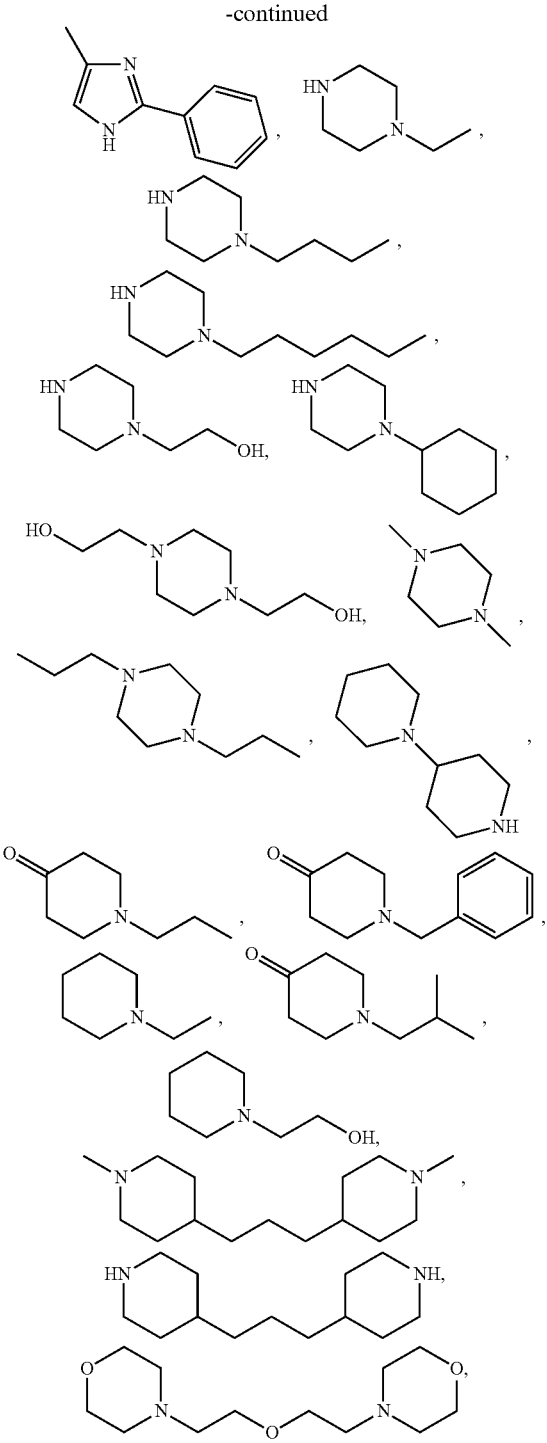

and tautomers and mixtures thereof.

The herbicide salts may be derived from carboxylic acid herbicides and a base compound (e.g., amine). As noted above, in one method, herbicide in free acid form is mixed with an amine in water or other suitable solvent.

Typically, when preparing the herbicide salts of the present invention from a carboxylic acid herbicide containing a single carboxylic acid moiety and a base compound containing a single amine functional group susceptible to forming a cation, equimolar or excess base is used. However, when using some base compounds that contain more than a single amine functional group (e.g., di- and tri-amines), equimolar or excess base compound may be unnecessary. With carboxylic acid herbicides containing more than one carboxylic acid moiety and/or base compounds containing more than one amine functional group, the relative proportions of base compound and herbicide free acid are adjusted as necessary. Accordingly, in various embodiments, the molar ratio of the base compound to carboxylic acid herbicide is typically at least about 0.4:1, at least about 0.5:1, at least about 0.6:1, at least about 0.7:1, at least about 0.8:1, at least about 0.9:1, at least about 1:1, at least about 1.1:1, at least about 1.2:1, at least about 1.3:1, at least about 1.4:1, at least about 1.5:1, at least about 1.6:1, at least about 1.7:1, at least about 1.8:1, at least about 1.9:1, or at least about 2:1. In these and other embodiments, the molar ratio of the base compound to carboxylic acid herbicide may range from about 0.4:1 to about 2:1, from about 0.5:1 to about 2:1, from about 0.7:1 to about 2:1, from about 0.8:1 to about 1.8:1, from about 1:1 to about 2:1, from about 1.2:1 to about 1.8:1, from about 0.5:1 to about 1.5:1, or from about 1:1 to about 1.5:1.

Stated in other terms, equimolar or excess cations (i.e., proton-accepting groups) are typically provided when preparing the herbicide salts of the present invention. Accordingly, in various embodiments the molar ratio of cations to carboxylic acid herbicide anions (i.e., proton-donating groups) is at least about 1:1, at least about 1.1:1, at least about 1.2:1, at least about 1.3:1, at least about 1.4:1, at least about 1.5:1, at least about 1.6:1, at least about 1.7:1, at least about 1.8:1, at least about 1.9:1, or at least about 2:1. In these and other embodiments, the molar ratio of cations to carboxylic acid herbicide anions may range from about 1:1 to about 2:1, from about 1:1 to about 1.8:1, from about 1.1:1 to about 2:1, from about 1.2:1 to about 1.8:1, or from about 1:1 to about 1.5:1.

In certain instances, water-soluble herbicide salts are desirable so that aqueous herbicidal solutions or formulations can be prepared. Accordingly, in various embodiments, the herbicide amine salts in accordance with the present invention are water-soluble such that they may be dissolved in an aqueous solution or formulated in an aqueous solution concentrate. In other instances, water-insoluble herbicide salts may be desirable. Therefore, in accordance with other embodiments, the herbicide salts in accordance with the present invention are water-insoluble such that they may be dissolved in an organic solvent or incorporated into an emulsion concentrate or suspension.

Suspensions of water-insoluble herbicide salts can be made by milling or grinding the dry herbicide salt in a milling machine such as an Eiger mill to the desired particle size (e.g., under 10 μm). Other adjuvants such as defoaming agents, dispersants, and stabilizers may be added during the milling process. Subsequently, the milled or ground herbicide salt particles are mixed with a liquid medium to form the suspension.

The herbicide salts of the present invention may be used in the preparation of herbicide formulations further comprising one or more additional co-herbicides. Co-herbicides include other carboxylic acid herbicides and salts thereof (e.g., auxin herbicide salts as previously described). Co-herbicides also include acetyl CoA carboxylase (ACCase) inhibitors, acetolactate synthase (ALS) or acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin transport inhibitors and nucleic acid inhibitors, salts and esters thereof; racemic mixtures and resolved isomers thereof; and combinations thereof. Specific examples of possible co-herbicides include 2,4-D, aminocyclopyrachlor, mecoprop, mecoprop-P, triclopyr, acetochlor, acifluorfen, alachlor, atrazine, azafenidin, bifenox, butachlor, butafenacil, carfentrazone-ethyl, diuron, dithiopyr, flufenpyr-ethyl, flumiclorac-pentyl, flumioxazin, fluoroglycofen, fluthiacet-methyl, fomesafen, glyphosate, glufosinate, imazethapyr, lactofen, metazochlor, metolachlor (and S-metolachlor), metribuzin, oxadiargyl, oxadiazon, oxyfluorfen, pretilachlor, propachlor, propisochlor, pyraflufen-ethyl, sulfentrazone and thenylchlor, and salts and esters thereof; racemic mixtures and resolved isomers thereof, and combinations thereof. In some embodiments, the co-herbicide is a photosystem II inhibitor selected from, for example, ametryn, amicarbazone, atrazine, bentazon, bromacil, bromoxynil, chlorotoluron, cyanazine, desmedipham, desmetryn, dimefuron, diuron, fluometuron, hexazinone, ioxynil, isoproturon, linuron, metamitron, methibenzuron, metoxuron, metribuzin, monolinuron, phenmedipham, prometon, prometryn, propanil, pyrazon, pyridate, siduron, simazine, simetryn, tebuthiuron, terbacil, terbumeton, terbuthylazine and trietazine, salts and esters thereof, and mixtures thereof. In another embodiment, the co-herbicide is a 4-HPPD inhibitor selected from, for example, mesotrione, isoxaflutole, benzofenap, pyrazolynate, pyrazoxyfen, sulcotrione, tembotrione, and tropramezone.

In accordance with another embodiment, the co-herbicide is a graminicide selected from butroxydim, clethodim, cycloxydim, sethoxydim, tepraloxydim, tralkoxydim, profoxydim, haloxyfop, propaquizafop and the $C_{1-4}$ alkyl and propargyl esters of clodinafop, cyhalofop, diclofop, fenoxaprop, fluazifop, fluazifop-P, haloxyfop, quizalofop and quizalofop-P (e.g., quizalofop-ethyl or quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl).

In various embodiments, the herbicide salts of the present invention (e.g., salts of dicamba and/or 2,4-D) are used in the preparation of an herbicidal formulation containing glyphosate or glufosinate or salts or esters thereof as a co-herbicide.

The herbicide salts of the present invention may be used in the preparation of concentrate, tank mix or ready-to-use (RTU) formulations. Tank mix and RTU formulations comprising one or more of the herbicide salts of the present invention and optionally one or more co-herbicides typically comprise from about 0.1 g a.e./L to about 50 g a.e./L total herbicide loading while concentrate formulations typically comprise from about 50 to about 750 g a.e./L, from about 300 to about 750 g a.e./L, from about 350 to about 750 g a.e./L, from about 400 to about 750 g a.e./L, from about 450 to about 750 g a.e./L, or even from about 500 to about 750 g a.e./L total herbicide loading (for example, 50, 100, 150, 200, 250, 300, 350, 400, 450, 500, 550, 600, 650, 700, or even 750 g a.e./L, and ranges thereof). In co-herbicide formulations, the weight ratio on an acid equivalent basis of the carboxylic acid herbicide amine salt to the total co-herbicide is typically no greater than about 50:1, for example, about 50:1, 25:1, 10:1, 5:1, 3:1, 2:1, 1:1, 1:2, 1:3, 1:5 or even 1:10 and ranges thereof (e.g., from about 50:1 to about 1:10, from about 50:1 to about 1:5, from about 50:1 to about 1:1, from about 50:1 to about 3:1, from about 50:1 to about 5:1, from about 50:1 to about 10:1, from about 25:1 to about 1:1, or from about 25:1 to about 3:1, on an acid equivalent basis).

The herbicide salts of the present invention may be formulated with other conventional adjuvants, excipients or additives known to those skilled in the art. These other additives or ingredients may be introduced into the compositions of the present invention to provide or improve certain desired properties or characteristics of the formulated product. Hence, the herbicidal composition may further comprise one or more additional ingredients selected from, without limitation, surfactants, foam-moderating agents, preservatives or anti-microbials, antifreeze agents, solubility-enhancing agents, dispersants, stabilizers, dyes, and thickening agents. For example, in various embodiments, the herbicidal composition comprising an herbicidal salt of the present invention, further comprises a surfactant selected from the group consisting of alkoxylated tertiary etheramines, alkoxylated quaternary etheramines, alkoxylated etheramine oxides, alkoxylated tertiary amines, alkoxylated quaternary amines, alkoxylated polyamines, sulfates, sulfonates, phosphate esters, alkyl polysaccharides, alkoxylated alcohols, and combinations thereof. The weight ratio of the carboxylic acid herbicide amine salt acid equivalent to surfactant can be readily determined by those skilled in the art (e.g., from about 1:1 to about 20:1, from about 2:1 to about 10:1 or from about 3:1 to about 8:1).

Application mixtures of the herbicides salts of the present invention may be prepared by dissolving the salts in water or other suitable solvent or by suitable dilution of a concentrate composition and applying to the foliage of unwanted plants by methods known in the art. The application mixture is applied to the foliage of a plant or plants at an application rate sufficient to give a commercially acceptable rate of weed control. This application rate is usually expressed as amount of herbicide per unit area treated, e.g., grams acid equivalent per hectare (g a.e./ha). Depending on plant species and growing conditions, the period of time required to achieve a commercially acceptable rate of weed control can be as short as a week or as long as three weeks, four weeks or 30 days. Application mixtures of the herbicides salts can be applied before planting, at planting, pre-emergence, or post-emergence to crop plants depending on the particular herbicide salt and crop plant.

Application mixtures prepared with the herbicide salts of the present invention may be applied to the foliage of crop plants and/or unwanted plants in the proximity of crop plants. Crop plants include hybrids, inbreds, and transgenic or genetically modified plants having specific traits or combinations of traits including, without limitation, herbicide tolerance (e.g., tolerant to carboxylic acid herbicides or other herbicides), *Bacillus thuringiensis* (Bt), high oil, high lysine, high starch, nutritional density, and drought resistance. Particular crop plants include, for example, corn, peanuts, potatoes, soybeans, canola, alfalfa, sugarcane, sugar beets, peanuts, grain sorghum (milo), field beans, rice, sunflowers, wheat and cotton. In various embodiments, the crop plant is selected from the group consisting of soybeans, cotton, peanuts, rice, wheat, canola, alfalfa, sugarcane, sorghum, and sunflowers. In other embodiments, the crop plant is selected from the group consisting of corn, soybean and cotton.

Herbicidal application mixtures prepared with herbicide salts of the present invention are particularly suited for application to transgenic plants having certain herbicide tolerance traits. In some embodiments, the crop plants are resistant to carboxylic acid herbicides (e.g., dicamba and/or 2,4-D) and/or other herbicides (e.g., glyphosate). For example, an application mixture comprising a dicamba salt or 2,4-D salt of the present invention would be especially suited for applying to the foliage of auxin-susceptible plants growing in and/or adjacent to a field of crop plants comprising transgenic crop plants having a dicamba tolerance trait or 2,4-D tolerance trait, respectively. Further, a spray formulation comprising a carboxylic acid herbicide salt of the present invention and a co-herbicide comprising glyphosate or glufosinate (or salts thereof) would be especially suited for applying to the foliage of carboxylic acid herbicide-susceptible plants and plants susceptible to the co-herbicide growing in and/or adjacent to a field of crop plants comprising transgenic crop plants having stacked carboxylic acid herbicide tolerance trait and a glyphosate or glufosinate tolerance trait, respectively.

Herbicidal application mixtures containing a herbicide salt of the present invention can be applied pre-planting of the crop plant, such as from about two to about three weeks before planting herbicide-susceptible crop plants or crop plants not having a herbicide tolerance trait. Crop plants that are not susceptible to carboxylic acid herbicides or certain co-herbicides, (e.g., corn with respect to auxin herbicides), or plants having carboxylic acid herbicide tolerance and co-herbicide tolerance traits typically have no pre-planting restriction and the application mixture can be applied immediately before planting such crops. The application mixture can be applied at planting, pre-emergence, or post-emergence to crop plants to control carboxylic acid herbicides-susceptible weeds and, if a co-herbicide is present, co-herbicide-susceptible weeds in a field of the crop plants.

As mentioned above, volatility is a known problem of application mixtures containing salts of many carboxylic acid herbicides. Without being bound by theory, in some instances, the salts of the present invention are believed to provide desirable low volatility and reduced associated offsite movement. It has been discovered that significant decreases in volatility may be realized when using the herbicide salts of the present invention. An application mixture containing a herbicide salt of the present invention may provide greater than about 20%, 30%, 40%, 50%, 60%, 65%, 75%, 80%, or 85% reduction in volatility when compared to a similar conventional herbicide mixtures.

Volatility reduction may be quantified experimentally by methods known in the art. In one method the volatility of solutions containing a herbicide salt can be measured in the gas phase (air) via tube tests. In a tube test, a sample of the herbicide solution is placed in a test tube that has been modified to allow air flow through the tube. A selective collection medium is attached to the outlet of the tube to collect volatilized herbicide. The collection medium is then analyzed for the respective herbicide. For further details see the Tube Test Protocol described in Example 2.

In another method, the volatility of solutions containing a herbicide salt can be evaluated by measuring herbicide concentrations in the gas phase (air) through air sampling in humidome plant growth chambers, which are maintained at constant temperature and humidity. For further details see the Humidome Protocol described in Example 2.

The term "hydrocarbyl" as used herein describes organic moieties consisting exclusively of the elements carbon and hydrogen and preferably containing 1 to about 50 carbon atoms, preferably 1 to about 30 carbon atoms, and even more preferably 1 to about 20 carbon atoms, including branched or unbranched, saturated or unsaturated and cyclic species. These moieties include alkyl, alkenyl, alkynyl, and aryl moieties optionally substituted with other aliphatic or cyclic hydrocarbon groups, such as alkaryl, alkenaryl and alkynaryl.

The term "substituted hydrocarbyl" as used herein describes hydrocarbyl moieties that are substituted with at least one atom other than carbon, including moieties in which a carbon chain or ring atom is substituted with a hetero atom such as nitrogen, oxygen, silicon, phosphorus, boron, sulfur, or a halogen atom. Unless otherwise stated, these substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are preferably lower alkyl containing from 1 to 20 carbon atoms in the principal chain. They may be straight or branched chain or cyclic and include methyl, ethyl, propyl, isopropyl, n-butyl, isobutyl, hexyl, 2-ethylhexyl, and the like.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl.

As used herein, the term "acid equivalent" or "a.e." refers to the amount of herbicide present without taking into account the weight of the counter-ion of the salt species present.

EXAMPLES

The following non-limiting examples are provided to further illustrate the present invention.

Example 1

In this example, various salts of dicamba were prepared as described below with dicamba acid and various base compounds as listed below in Table 1.

Various dicamba salts were prepared by mixing water and amine base reagents for a few minutes followed by addition of dicamba acid in one portion. The amount of dicamba acid added was pre-calculated based on the desired molar ratio of amine base compound to dicamba acid. The resulting mixtures were stirred for a period of time (e.g., from about 1 to about 24 hours) until all of the solids had dissolved by visual inspection. In some instances, heating of the reaction mixture was necessary to increase the reaction rate or facilitate completion of the reaction.

Various dicamba salts were also prepared according to the method described above, with the exception that the water was replaced by a suitable organic solvent (e.g., methanol). The amine base reagents and dicamba acid were dissolved in the solvent. The mixtures were stirred for at least for 2 hours in order to facilitate completion of the reaction. After reaction, the solvent was removed from the reaction mixture by either heating, application of vacuum, or the combination of both.

TABLE 1

| Salt No. | Base Compound | Approximate Base Compound to Dicamba Acid Molar Ratio | Solvent |
|---|---|---|---|
| 1 | 1-cycloheyxlpiperazine | 1:1 | Methanol |
| 2 | 1-cycloheyxlpiperazine | 0.67:1 | Methanol |
| 3 | 1-cycloheyxlpiperazine | 1:1 | Water |
| 4 | 1-(2-hydroxyethyl)piperazine | 1:1 | Water |
| 5 | 1-n-butylpiperazine | 1:1 | Water |
| 6 | 1-ethylpiperazine | 1:1 | Water |
| 7 | 1-ethylpiperazine | 0.67:1 | Water |
| 8 | 4-methylimidazole | 1:1 | Water |
| 9 | 2-isopropylimidazole | 1:1 | Water |
| 10 | 2-ethyl-4-methylimidazole | 1:1 | Water |
| 11 | 2-ethylimidazole | 1:1 | Water |
| 12 | 2-methylimidazole | 1:1 | Water |
| 13 | 2-phenylimidazole | 1:1 | Methanol |
| 14 | 2-phenyl-4-methylimidazole | 1:1 | Methanol |
| 15 | 1-ethylpiperidine | 1:1 | Water |
| 16 | 1-n-propylpiperidin-4-one | 1.1:1 | Water |

TABLE 1-continued

| Salt No. | Base Compound | Approximate Base Compound to Dicamba Acid Molar Ratio | Solvent |
|---|---|---|---|
| 17 | 1-isobutylpiperidin-4-one | 1:1 | Water |
| 18 | 1-(2-hydroxyethyl)piperidine | 1:1 | Water |
| 19 | 4-piperidinopiperidine | 0.5:1 | Water |
| 20 | 1-benzylpiperidin-4-one | 1:1 | Methanol |
| 21 | 4,4'-trimethylene-bis(1-methylpiperidine) | 0.5:1 | Water |
| 22 | 4,4'-trimethylenedipiperidine | 0.5:1 | Water |
| 23 | 1,4-dimethylpiperazine | 1:1 | Water |
| 24 | 1,4-bis(2-hydroxyethyl)piperazine | 1:1 | Water |
| 25 | 4,4'-(oxydi-2,1-ethanediyl)bismorpholine | 0.69:1 | Water |

Example 2

In this example, various salts of dicamba prepared in Example 1 were selected for volatility testing. As described below, spray solutions containing the selected dicamba salts were prepared and subjected to volatility testing via the tube test and/or humidome protocols. Typically, the spray solutions containing the selected dicamba salts also contained potassium glyphosate co-herbicide. Aqueous test spray solutions containing selected salts of dicamba and potassium glyphosate were prepared by mixing a solution of dicamba salt with a solution of potassium glyphosate salt and adjusting the relative proportion and/or diluting with water to arrive at the desired concentration of dicamba and glyphosate.

Tube Test Protocol

To measure the dicamba concentration in the gas phase (air) volatilized from the spray solutions, 10 mL samples of each solution were placed into a 50 mL plastic centrifuge tube with one hole approximately ⅛ in (3.2 mm) diameter drilled into the tube at the mark between 20 mL and 30 mL lines. A 22 mm×30 mm polyurethane foam (PUF), cut from a 76 mm length, available from SKC Inc., catalog #P22692, was placed into a glass tube of approximately 20 mm diameter with parafilm wrapped around the outside to obtain a snug fit into the top of the centrifuge tube. A hose was connected to the other end of the glass tube leading to a vacuum line. The air flow was regulated to approximately 2 L/min using a flow controller. Air was pulled through the tube at approximately 2 L/min for 24 hours. Note that the air conditions of flow rate, temperature, pressure and composition (e.g., relative humidity) are not narrowly critical as long as the various samples are analyzed under similar conditions. For instance, air at from about 5° C. to about 40° C., from about 0.5 to about 1.5 bar pressure, from about 0% to about 95% relative humidity, and at a flow rate of from about 0.1 to 10 L/min-mL sample could be suitably used for volatility analysis. In this test, the air pulled through the tubes was at about 35° C. and about 40% relative humidity. The PUF was removed from the glass tube, extracted with 20 mL methanol and the resulting solution analyzed for dicamba concentration using liquid chromatography-mass spectroscopy (LC-MS) methods known in the art.

For comparison, samples of spray solutions containing 2 wt. % a.e. of the diglycolamine salt of dicamba (i.e., CLARITY) were also subjected to the tube test protocol. The comparison spray solution did not contain potassium herbicide co-herbicide.

The results of the tube tests are presented in Table 2. The reduction in volatility is calculated relative to the volatility of the samples containing the diglycolamine salt of dicamba.

Humidome Protocol

Humidomes were obtained from Hummert International (Part Nos 14-3850-2 for humidomes and 11-3050-1 for 1020 flat tray) and modified by cutting a 2.2 cm diameter hole on one end approximately 5 cm from the top to allow for insertion of a glass air sampling tube (22 mm OD) containing a polyurethane foam (PUF) filter. The sampling tube was secured with a VITON o-ring on each side of the humidome wall. The air sampling tube external to the humidome was fitted with tubing that was connected to a vacuum manifold immediately prior to sampling.

The flat tray beneath the humidome was filled with 1 liter of sifted dry or wet 50/50 soil (50% Redi-Earth and 50% US 10 Field Soil) to a depth of about 1 cm. To measure the dicamba concentration in the gas phase (air) volatilized from the spray solutions, samples of the spray solutions were sprayed over the soil in the humidome using a track sprayer at a rate of 10 gallons per acre (GPA). To avoid contamination of the sides of the flat tray, each tray was nested in an empty tray prior to spraying.

The flat tray bottom containing the dicamba formulation on soil was covered with a humidome lid and the lid was secured with clamps. The assembled humidomes were placed in a temperature and humidity controlled environment and connected to a vacuum manifold through the air sampling line. Air was drawn through the humidome and PUF at a rate of 2 liters per minutes (LPM) for 24 hours at which point the air sampling was stopped. The humidomes were then removed from the controlled environment and the PUF filter was removed. The PUF filter was extracted with 20 mL of methanol and the solution was analyzed for dicamba concentration using LC-MS methods known in the art.

For comparison, samples of spray solutions containing the diglycolamine salt of dicamba (i.e., CLARITY) at approximately the same weight percent a.e. as the tested dicamba salt sprays were subjected to the humidome tests. The comparison spray solution did not contain potassium herbicide co-herbicide.

The results of the humidome tests are presented in Table 2. The reduction in volatility is calculated relative to the volatility of the samples containing the diglycolamine salt of dicamba.

The results of the volatility tests show that the selected dicamba salts were significantly less volatile than the solutions containing DGA dicamba.

TABLE 2

| Dicamba Salt No. | Dicamba Salt Concentration (wt. % a.e.) | Potassium Glyphosate Concentration (wt. % a.e.) | Volatility Reduction Over DGA Dicamba Spray (%) | |
|---|---|---|---|---|
| | | | Tube Test | Humidome Test |
| 3 | 2 | 6 | 75 | — |
| 4 | 2 | 6 | 69 | — |
| 5 | 2 | 6 | 70 | — |
| 6 | 2 | 6 | 83 | — |
| 7 | 2 | 6 | 42 | — |
| 9 | 0.6 | 0.9 | — | 63 |
| 9 | 0.6 | 1.2 | — | 67 |
| 9 | 2 | 6 | 65 | — |
| 10 | 10 | — | 88 | — |
| 10 | 2 | 6 | 72 | — |
| 10 | 0.6 | 0.9 | — | 86 |
| 10 | 0.6 | 1.2 | — | 85 |
| 10 | 2.4 | 4.8 | | 86 |
| 11 | 0.6 | 0.9 | — | 67 |
| 11 | 0.6 | 1.2 | — | 60 |
| 11 | 2 | 6 | 67 | — |
| 12 | 0.6 | 0.9 | — | 46 |
| 12 | 0.6 | 1.2 | — | 50 |
| 14 | 0.6 | 0.9 | — | 92 |
| 16 | 2 | 6 | 20 | — |
| 17 | 2 | 6 | 57 | — |
| 19 | 2 | 6 | 23 | — |
| 20 | 2 | 6 | 42 | — |
| 22 | 2 | 6 | 60 | — |
| 22 | 0.6 | 0.9 | — | 68 |
| 23 | 2 | 6 | 23 | — |
| 24 | 2 | 6 | 57 | — |
| 24 | 0.6 | 0.9 | — | 76 |
| 25 | 2 | 6 | 70 | — |
| 25 | 0.6 | .9 | — | 76 |

—: Not tested or not present

Example 3

In this example, the herbicidal effectiveness of selected dicamba salts prepared in accordance with Example 1 was evaluated in greenhouse testing. The herbicidal effectiveness data set forth herein report "Weed killing efficacy" as a percentage following a standard procedure in the art which reflects a visual assessment of plant mortality and growth reduction by comparison with untreated plants, made by technicians specially trained to make and record such observations. Such measurements are relied upon and regularly reported by Monsanto Company in the course of its herbicide business.

The following procedure was used for testing compositions of this example to determine herbicidal effectiveness.

Seeds of velvetleaf (ABUTH) were planted in 85 mm square pots in a soil mix which was previously steam sterilized and prefertilized with a 14-14-14 NPK slow release fertilizer at a rate of 3.6 kg/m$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 21° C. during the night. Plants were sub-irrigated throughout the test to ensure adequate soil moisture levels.

Application of herbicide salt solutions were made by spraying with a track sprayer fitted with a 9501E nozzle calibrated to deliver a spray volume of approximately 38 liters per hectare (l/ha). After treatment, pots were returned to the greenhouse until ready for evaluation.

For evaluation of herbicidal effectiveness, all plants in the test were examined by a single practiced technician, who recorded percent control, a visual measurement of the effectiveness of each treatment by comparison with untreated plants. Weed killing efficacy of 0% indicates no effect, and efficacy of 100% indicates that all of the plants are completely dead. Control of 85% or more is in most cases considered acceptable for normal herbicide use. However, in greenhouse tests such as those for this example it is normal to apply compositions at rates which give less than 85% control, as this makes it easier to discriminate among compositions having different levels of effectiveness. The weed killing efficacy was evaluated 21 days after the treatment. The table below lists the results of three imidazolium dicamba salts compared to CLARITY. The results show there is no significant difference between the imidazolium dicamba salts and CLARITY for weed control.

TABLE 3

| | Application rate (g a.e./ha) | | |
|---|---|---|---|
| | 140 | 280 | 560 |
| Dicamba salt | Weed killing efficacy (%) | | |
| diglycolamine dicamba (CLARITY) | 43.3 | 68.8 | 86.7 |
| 2-ethyl-4-methyl imidazolium dicamba | 30.0 | 62.5 | 83.3 |
| 2-methyl imidazolium dicamba | 40.0 | 66.7 | 85.0 |
| 2-ethyl imidazolium dicamba | 38.3 | 67.5 | 80.8 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A herbicide salt comprising an anion of an auxin herbicide and a cation of a compound selected from the group consisting of:

(a) Formula I:

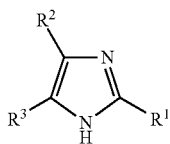

Formula I wherein $R^1$ is substituted or unsubstituted $C_1$-$C_{20}$ alkyl, substituted or unsubstituted $C_1$-$C_{20}$ alkanol, substituted or unsubstituted $C_5$-$C_{20}$ cycloalkyl, substituted or unsubstituted $C_3$-$C_{20}$ heterocycloalkyl, substituted or unsubstituted aryl, or substituted or unsubstituted heteroaryl, and $R^2$ and $R^3$ are independently hydrogen or substituted or unsubstituted hydrocarbyl;

(b) Formula II:

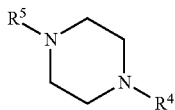

Formula II wherein $R^4$ and $R^5$ are independently hydrogen or substituted or unsubstituted hydrocarbyl, provided that when $R^5$ is hydrogen or an unsubstituted $C_1$-$C_6$ alkyl, then $R^4$ is not an aminoalkyl or when $R^4$ is hydrogen or an unsubstituted $C_1$-$C_6$ alkyl, then $R^5$ is not an aminoalkyl;

(c) Formula III:

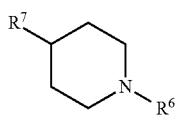

Formula III wherein $R^6$ is hydrogen, substituted or unsubstituted $C_1$-$C_{20}$ alkyl, substituted or unsubstituted $C_1$-$C_{20}$ alkanol, substituted or unsubstituted $C_5$-$C_{20}$ cycloalkyl, substituted or unsubstituted $C_3$-$C_{20}$ heterocycloalkyl, substituted or unsubstituted aryl, substituted or unsubstituted alkylaryl, or substituted or unsubstituted heteroaryl and $R^7$ is hydrogen, oxo, or unsubstituted or substituted hydrocarbyl, provided that when $R^6$ is an unsubstituted $C_1$-$C_6$ alkyl, then $R^7$ is not an aminoalkyl or when $R^7$ is hydrogen or an unsubstituted $C_1$-$C_6$ alkyl, then $R^6$ is not an aminoalkyl;

(d) Formula IV:

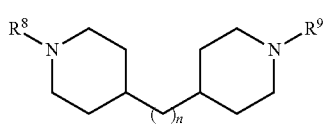

Formula IV wherein n is from 1 to about 20, from 1 to about 10, from about 3 to about 10, or from about 3 to about 6 and $R^8$ and $R^9$ are independently any substituent as defined for $R^7$;

(e) Formula V:

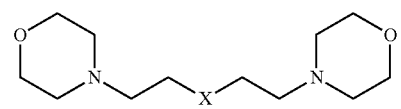

Formula V wherein X is O, $NR^{10}$ or S and $R^{10}$ is hydrogen or $C_{1-6}$ alkyl; and tautomers and mixtures thereof.

2. The herbicide salt of claim 1 comprising a cation of the compound of Formula I.

3. The herbicide salt of claim 2 wherein $R^2$ and $R^3$ are independently hydrogen, substituted or unsubstituted $C_1$-$C_{20}$ alkyl, substituted or unsubstituted $C_1$-$C_{20}$ alkanol, substituted or unsubstituted $C_5$-$C_{20}$ cycloalkyl, substituted or unsubstituted $C_3$-$C_{20}$ heterocycloalkyl, substituted or unsubstituted aryl, or substituted or unsubstituted heteroaryl.

4. The herbicide salt of claim 1 comprising a cation of the compound of Formula II.

5. The herbicide salt of claim 4 wherein $R^4$ and $R^5$ are independently substituted or unsubstituted $C_1$-$C_{20}$ alkyl, substituted or unsubstituted $C_1$-$C_{20}$ alkanol, substituted or unsubstituted $C_3$-$C_{20}$ cycloalkyl, substituted or unsubstituted $C_1$-$C_{20}$ heterocycloalkyl, substituted or unsubstituted aryl, or substituted or unsubstituted heteroaryl, provided that when $R^5$ is an unsubstituted $C_1$-$C_6$ alkyl, then $R^4$ is not an aminoalkyl or when $R^4$ is an unsubstituted $C_1$-$C_6$ alkyl, then $R^5$ is not an aminoalkyl.

6. The herbicide salt of claim 1 comprising a cation of the compound of Formula III.

7. The herbicide salt of claim 6 wherein $R^6$ is a substituted or unsubstituted $C_1$-$C_{10}$ alkyl, substituted or unsubstituted $C_1$-$C_{10}$ alkanol, substituted or unsubstituted $C_5$-$C_{10}$ cycloalkyl, substituted or unsubstituted $C_3$-$C_{10}$ heterocycloalkyl, substituted or unsubstituted aryl, substituted or unsubstituted alkylaryl, or substituted or unsubstituted heteroaryl.

8. The herbicide salt of claim 1 comprising a cation of the compound of Formula IV.

9. The herbicide salt of claim 1 comprising a cation of a compound of Formula V.

10. The herbicide salt of claim 1 comprising the cation of a compound selected from the group consisting of:

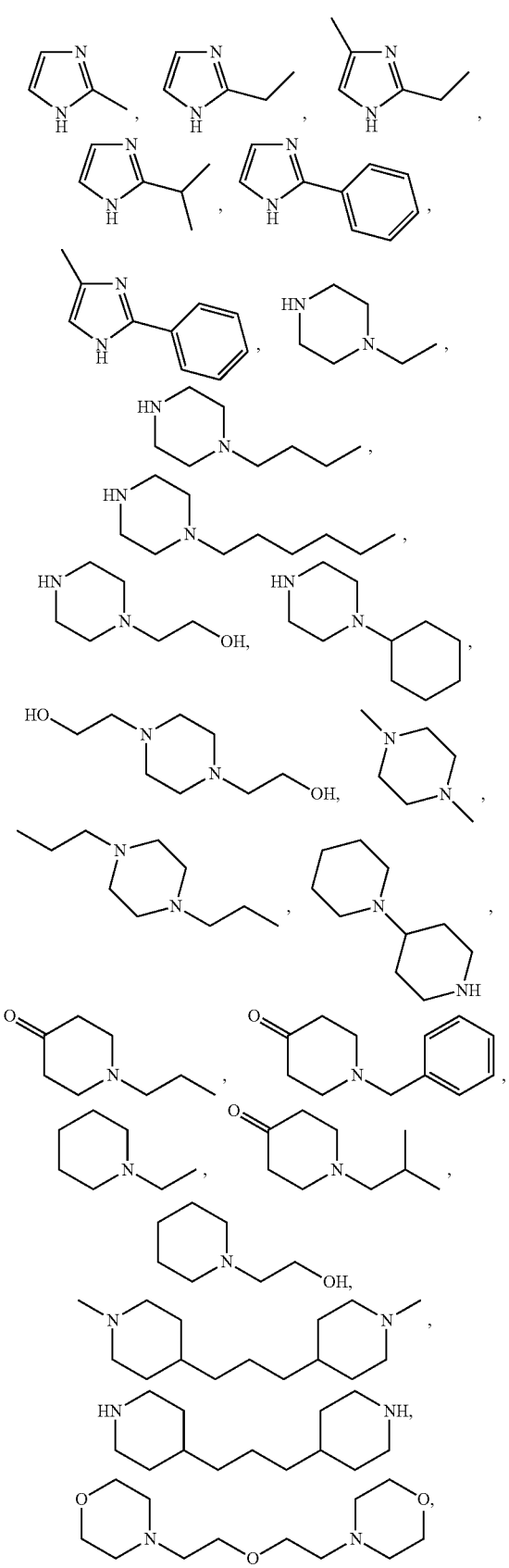

tautomers thereof, and mixtures thereof.

11. The herbicide salt of claim 1 wherein the auxin herbicide comprises at least one herbicide selected from the group consisting of 3,6-dichloro-2-methoxybenzoic acid (dicamba); 2,4-dichlorophenoxyacetic acid (2,4-D); 4-(2,4 dichlorophenoxy)butanoic acid (2,4-DB); 2-(2,4-dichloro-phenoxy)propanoic acid (dichloroprop); 2-(4-chloro-2-methylphenoxy)acetic acid (MCPA); 4-(4-chloro-2-methyl-phenoxy)butanoic acid (MCPB); 4-amino-3,6-dichloro-2-pyridinecarboxylic acid (aminopyralid); 3,6-dichloro-2-pyridinecarboxylic acid (clopyralid); 2-[(4-amino-3,5-dichloro-6-fluoro-2-pyridinyl)oxy]acetic acid (fluroxypyr); [(3,5,6-trichloro-2-pyridinyl)oxy]acetic acid (triclopyr); 2-(4-chloro-2-methylphenoxy)propanoic acid (mecoprop); 4-amino-3,5,6-trichloro-2-pyridinecarboxylic acid (picloram); 3,7-dichloro-8-quinolinecarboxylic acid (quinclorac); 6-amino-5-chloro-2-cyclopropyl-4-pyrimidinecarboxylic acid (aminocyclopyrachlor) and combinations thereof.

12. The herbicide salt of claim 1 wherein the auxin herbicide comprises 3,6-dichloro-2-methoxybenzoic acid (dicamba) or 2,4-dichlorophenoxyacetic acid (2,4-D).

13. A herbicidal application mixture useful for killing or controlling the growth of unwanted plants comprising the herbicidal salt of claim 1.

14. The herbicidal application mixture of claim 13 further comprising at least one surfactant wherein the weight ratio of the herbicidal salt acid equivalent to surfactant is from about 1:1 to about 20:1.

15. The herbicidal application mixture of claim 13 further comprising at least one co-herbicide selected from the group consisting of auxin herbicides and salts thereof; acetyl CoA carboxylase (ACCase) inhibitors, acetolactate synthase (ALS) or acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin transport inhibitors, nucleic acid inhibitors, and salts and esters thereof; racemic mixtures and resolved isomers thereof; and combinations thereof.

16. The herbicidal application mixture of claim 13 further comprising at least one co-herbicide selected from: 2,4-D, aminocyclopyrachlor, mecoprop, mecoprop-P, triclopyr, acetochlor, acifluorfen, alachlor, atrazine, azafenidin, bifenox, butachlor, butafenacil, carfentrazone-ethyl, diuron, dithiopyr, flufenpyr-ethyl, flumiclorac-pentyl, flumioxazin, fluoroglycofen, fluthiacet-methyl, fomesafen, glyphosate, glufosinate, imazethapyr, lactofen, metazochlor, metolachlor (and S-metolachlor), metribuzin, oxadiargyl, oxadiazon, oxyfluorfen, pretilachlor, propachlor, propisochlor, pyraflufen-ethyl, sulfentrazone and thenylchlor, and salts and esters thereof; racemic mixtures and resolved isomers thereof, and combinations thereof.

17. The herbicidal application mixture of claim 13 wherein the co-herbicide comprises glyphosate or a salt or ester thereof.

18. A method of controlling unwanted plants comprising applying the herbicidal application mixture of claim 13 to the unwanted plants.

19. A method of controlling carboxylic acid herbicide-susceptible plants growing in and/or adjacent to a field of crop plants comprising applying the herbicidal application mixture of claim 13 to the foliage of the carboxylic acid herbicide-susceptible plants.

20. The method of claim 19 wherein the crop plant comprises a transgenic crop plant comprising a herbicide tolerant trait selected from the group consisting of a dicamba tolerance trait, a 2,4-D tolerance trait, a glyphosate tolerance trait, a glufosinate tolerance trait, and combinations thereof.

21. The herbicide salt of claim 3 wherein $R^2$ and $R^3$ are independently hydrogen or substituted or unsubstituted $C_1$-$C_{10}$ alkyl.

22. The herbicide salt of claim 21 wherein $R^1$ is a substituted or unsubstituted $C_1$-$C_{10}$ alkyl, substituted or unsubstituted $C_1$-$C_{10}$ alkanol, substituted or unsubstituted $C_5$-$C_{10}$ cycloalkyl, substituted or unsubstituted $C_3$-$C_{10}$ heterocycloalkyl, substituted or unsubstituted aryl, or substituted or unsubstituted heteroaryl.

23. The herbicide salt of claim 22 wherein $R^1$ is a $C_1$-$C_6$ alkyl, $C_1$-$C_6$ alkanol, $C_5$-$C_6$ cycloalkyl, or aryl.

24. The herbicide salt of claim 23 wherein $R^1$ is methyl, ethyl, isopropyl or phenyl.

\* \* \* \* \*